United States Patent [19]

Bowling

[11] Patent Number: 4,554,171

[45] Date of Patent: Nov. 19, 1985

[54] PROCESS FOR COATING RICE SEED WITH CALCIUM PEROXIDE BY CHEMICAL REACTION ON THE SEED

[76] Inventor: Clarence C. Bowling, 1750 Wooten Rd., Beaumont, Tex. 77707

[21] Appl. No.: 497,112

[22] Filed: May 23, 1983

[51] Int. Cl.⁴ .................................................. A01C 1/06
[52] U.S. Cl. .......................................... 427/4; 47/57.6
[58] Field of Search ...................... 427/4, 212; 47/57.6

[56] References Cited

U.S. PATENT DOCUMENTS 4,344,979  8/1982  Gago et al. .............................. 427/4

*Primary Examiner*—Michael R. Lusignan

[57] ABSTRACT

A process for coating rice seed with calcium peroxide whereby seeds are first coated with hydrogen peroxide by mixing and tumbling. As calcium hydroxide is added to the tumbling seed mass a chemical reaction takes place forming calcium peroxide, plus water and heat. The excess moisture and heat escapes from the seed mass as tumbling continues, resulting in a uniform coat of dry hard calcium peroxide on the seed.

3 Claims, No Drawings

PROCESS FOR COATING RICE SEED WITH CALCIUM PEROXIDE BY CHEMICAL REACTION ON THE SEED

BACKGROUND OF THE INVENTION

This invention relates to a process to coat rice seed with calcium peroxide. Rice seeds coated with calcium peroxide offers an improved method of establishing stands of rice plants in flooded seed beds with low oxygen levels. Calcium peroxide reacts with water to release oxygen that is utilized in germination by the coated seeds. Seeds of undesirable plants in the same seed bed will not germinate resulting in rice fields free of weeds. The usefulness of seed coated with calcium peroxide to establish stands of rice in flooded seed beds has been reported by Yamada, 1951; Ohta and Nakamura, 1970; Ohta and Makayama, 1971; Mitsuishi and Nakamura, 1977; Mikkelson, 1980 and Bowling and Turner 1980.

Calcium peroxide is a light fluffy powder which can be formulated by reacting calcium hydroxide with hydrogen peroxide. The reaction is as follows: $Ca(OH)_2 + H_2O_2 \rightarrow CaO_2 + 8 H_2O + heat$. The excess heat must be removed by cooling and the excess water by drying. The calcium peroxide must then be ground to the desired particle size. Each process adds to the cost of the product.

The process normally used to coat rice seed with calcium peroxide is to apply to the seed as a slurry in water or first apply an adhesive to the seed and then apply as a dry powder.

In view of the above considerations a process to coat rice seed with calcium peroxide by chemical reaction directly on the seed thereby eliminating the numerous steps required in the normal manufacturing and coating processes would be extremely beneficial in rice production.

SUMMARY

This invention relates to a process for coating rice seed with calcium peroxide by reacting hydrogen peroxide with calcium hydroxide on the seed surfaces and to improvements there in for improving its usefulness.

The primary object of the invention is to provide a process to coat seed with calcium peroxide by chemical reaction of hydrogen peroxide with calcium hydroxide directly on the surfaces of rice seed.

A further object of the invention is to provide a process to coat rice seed with calcium peroxide whereby hydrogen peroxide is first utilized to destroy harmful micro-organisms indigenous to the rice seed surfaces.

A still further object of the invention is to provide a process to coat rice seed with calcium peroxide whereby the excess heat, released when hydrogen peroxide is reacted with calcium hydroxide; is first absorbed by the seed mass and then slowly released thereby driving off excess moisture resulting in a uniform coating of dry, hard calcium peroxide on the seed.

Formulation directly on the seed eliminates the cooling, drying and grinding process necessary in regular manufacturing of calcium peroxide. Formulation directly on the seed simplifies the difficult problem of apply a fluffy powder to the seed. Formulation directly on the seed eliminates the necessity of removal of excess moisture required when calcium peroxide is applied as a slurry and no adhesive is required with this method of coating. Formulation directly on the seeds allow the utilization of the hydrogen peroxide to destroy harmful microrganisms present on the seed before reaction with calcium hydroxide.

DESCRIPTION OF THE PROCESS

Formulation of calcium peroxide directly on rice seed is accomplished by metering the required amount of hydrogen peroxide on the seed as they are continuously tumbled, mixed or blended by any of the various machines designed for treating seeds. After the seeds are covered with hydrogen peroxide, calcium hydroxide is added as the mixing blending process is continued. As the chemical reaction takes place the heat produced is absorbed by the moving grain mass and then gradually released. The mixing is continued as a hard dry uniform coat of calcium peroxide is formed on each seed.

The process as described is the most effective procedure for formulating calcium peroxide on seed rice. However, similar but less efficient results can be obtained by sticking the calcium hydroxide to the seed before adding the hydrogen peroxide or the two chemicals can be mixed rapidly and added to the seed before the chemical reaction occurs. It is to be understood that this patent also includes these procedures.

Calcium peroxide may also be formulated by reacting calcium nitrate with and alkali plus hydrogen peroxide. The reactions is as follows: $Ca(NO_3)_2 + H_2O_2 + 2 N_2OH \rightarrow CaO_2 - 2 Na NO_3 + 2 H_2O$. It is to be understood that his patent also include coating seed with calcium peroxide utilizing the above reaction.

It is also intended that this patent include all other seeds that might benefit from a coating of calcium peroxide.

I claim:

1. A process wherein a coating of calcium peroxide is formed on seed surfaces by chemical reaction of successive applications of hydrogen peroxide with calcium hydroxide.

2. A process of claim 1 wherein said hydrogen peroxide is applied to the seed first and is utilized to destroy harmful micro-organisms on the seed surfaces.

3. A process of claim 1 wherein heat produced by the said chemical reaction is utilized to assist in drying the calcium peroxide coating on the seed.

* * * * *